US00PP33759P3

(12) United States Plant Patent
Piriz

(10) Patent No.: US PP33,759 P3
(45) Date of Patent: Dec. 21, 2021

(54) RASPBERRY PLANT NAMED 'R15-21-5'

(50) Latin Name: *Rubus idaeus* L.
Varietal Denomination: R15-21-5

(71) Applicant: Fresas Nuevos Materiales S.A., Huelva (ES)

(72) Inventor: Antonio Refoyo Piriz, Huelva (ES)

(73) Assignee: Fresas Nuevos Materiales S.A., Huelva (ES)

( * ) Notice: Subject to any disclaimer, the term of this patent is extended or adjusted under 35 U.S.C. 154(b) by 0 days.

(21) Appl. No.: 16/501,887

(22) Filed: Jun. 28, 2019

(65) Prior Publication Data

US 2020/0413585 P1 Dec. 31, 2020

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
CPC ..... A01H 5/0887
See application file for complete search history.

(56) References Cited

U.S. PATENT DOCUMENTS

PP25,245 P3 1/2015 Pierron-Darbonne

OTHER PUBLICATIONS

PLUTO UPOVROM Plant Variety Database Sep. 24, 2020 Citation as per QZ PBR 20180640; Mar. 2, 2018; 1 page.*
Community Plant Variety Office (CPVO) Application/Registration No. 2018/0640, filed in the European CPVO on Mar. 1, 2018, and publicly available on Jun. 15, 2018.

* cited by examiner

*Primary Examiner* — Kent L Bell
(74) *Attorney, Agent, or Firm* — Cooley LLP

(57) ABSTRACT

The present invention provides a new and distinct raspberry plant designated as 'R15-21-5'. The new raspberry cultivar is distinguished from other cultivars by its combination of traits which include very early production on primocanes, branching habit, large light red colored fruit, trapezoidal shaped and fruits suitable for fresh consumption.

10 Drawing Sheets

Latin name of the genus and species: *Rubus idaeus* L.
Varietal denomination: 'R15-21-5'.

CROSS REFERENCE TO RELATED APPLICATIONS

This application relates to Community Plant Variety Office (CPVO) Application/Registration Number 2018/0640, filed in the Europe on Mar. 1, 2018, and the National Service of Certification and Identification of Seeds (SNICS) Application/Registration Number CP-2373, filed in the Mexico on Jun. 28, 2019, both applications of which are herein entirely incorporated by reference for all purposes.

BACKGROUND OF THE INVENTION

The present invention relates to a new and distinct primocane raspberry variety designated as 'R15-21-5'.

'R15-21-5' was obtained from seed produced by bees pollination of seedlings and was first fruited in Gibraleón (Huelva, Spain) growing fields in 2015. From the seedling and during testing, the plant was designated 'R15-21-5'. Seed female parent 'R14-21' (SD.10.82.6 x 'Tulameen') was an unpatented seedling grown in a controlled area with other seedlings and selected for its combination of favorable characteristics on primocane production. The male parent is unknown.

The new variety 'R15-21-5' was asexually propagated by root cuttings in a controlled environment at Gibraleón, Huelva, Spain. Asexual propagules from the original source have been tested in Cartaya, Moguer and Palos de la Frontera (Huelva, Spain) growing fields and to a limited extent. The properties of this variety were found to be transmissible by such asexual reproduction. This cultivar is stable and reproduces true to type in successive generations of asexual reproduction.

SUMMARY OF THE INVENTION

This invention concerns a new and distinct cultivar of primocane raspberry variety. The varietal denomination of the new variety is 'R15-21-5'. The new raspberry cultivar 'R15-21-5' is distinguished from other cultivars by its combination of traits which include very high production from October to January on primocanes and from April to June on floricanes; semi-upright branched plant; the vigour of the plant is medium-high, the fruit color is light red, trapezoidal-shaped, firm fruit and large size. The cultivar shows a very early cropping season production in protected culture.

BRIEF DESCRIPTION OF THE DRAWING

The accompanying colour photographs and traits show typical specimens of the new cultivar at various stages of development as nearly true as it is possible to make in colour reproductions. The pictures were taken during 2018 in Huelva, Spain.

DETAILED DESCRIPTION OF THE INVENTION

This invention relates to a new and distinctive primocane raspberry cultivar named 'R15-21-5'.

'R15-21-5' is a semi-upright, medium-high vigorous plant with some branches that produces large fruit size, light red colored and trapezoidal shape.

Fruit production season is much earlier than other cultivars when grown in protected culture, this allows large quantities of fruits in winter and early spring. Fruit is easily removed from its receptacle, with adequate width of the cavity, and easily visible on branches.

'R15-21-5' has not been noted to be sensitive to any pest in Huelva (Spain). Specifically, it is relatively tolerant to aphids and spider mites.

Plants of 'R15-21-5' are slightly susceptible to powdery mildew (*Podosphaera aphanis*) when greenhouse grown.

'R15-21-5' can be asexually propagated by root suckers, root cuttings and other known methods of propagating raspberry plants. No off-type plants have been observed in the history of asexual propagation of this cultivar by either method.

'R15-21-5' is distinguished from seed parent 'R14-21' and 'Tulameen' by the following characteristics:

Plant. 'R15-21-5' shows less vigor than seed parent 'R14-21' and a greater number of lateral branches than 'Tulameen'.

Current season's cane. 'R15-21-5' shows less cane diameter than 'R14-21' and 'Tulameen'.

Fruit. 'R15-21-5' shows large light red coloured fruit with a trapezoidal shape, and 'R14-21' fruit is smaller and the color is darker. Fruit color and shape of fruit is similar to those of 'Tulameen' but 'R15-21-5' shows larger fruits.

Spines. 'R15-21-5' shows less spine density and the spines are smaller than the spines in 'R14-21'.

'R15-21-5' is distinguished from other commercial cultivars by the following characteristics:

General. The onset of flowering on current season's canes in 'R15-21-5' begins 100 to 110 days after roots are planted in July. This is earlier than other commercial varieties such as 'Heritage' (unpatented variety), which flowers on current season's canes 140 to 150 days after planting in July; or, 'Adelita' (U.S. Plant Pat. No. 25,245 P3), which flowers on current season's canes 130 to 140 days after roots are planted in July.

Root. 'R15-21-5' shows a denser and thinner root system than 'Heritage' or 'Adelita'.

Plant. 'R15-21-5' is more vigorous and shows a greater number of branches than 'Heritage' or 'Adelita'. Branches of 'R15-21-5' are thicker than those of 'Adelita'.

Figure 1:
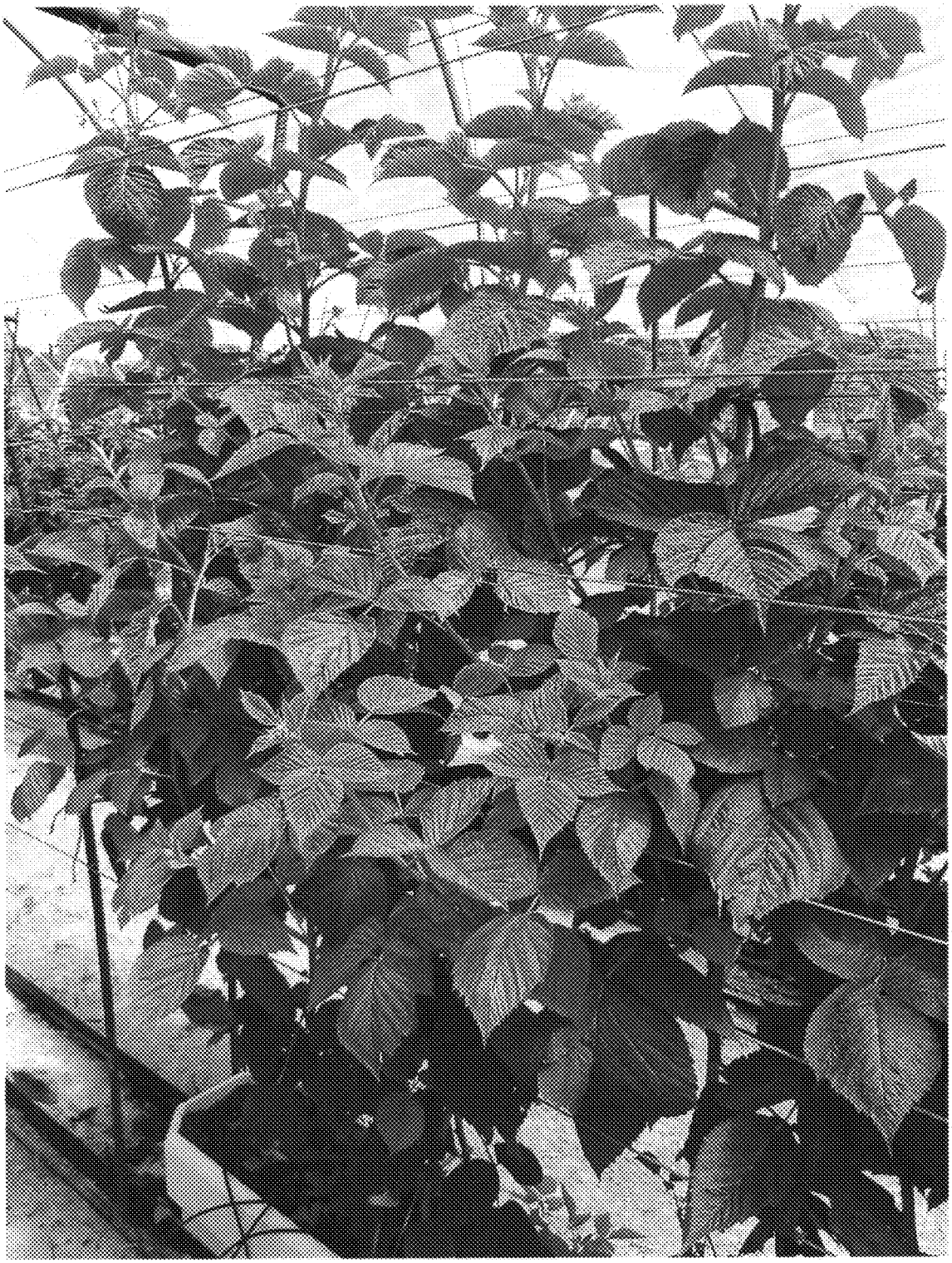
FIG. 1 shows plant habit, 140 days after planting date.
Figure 2:
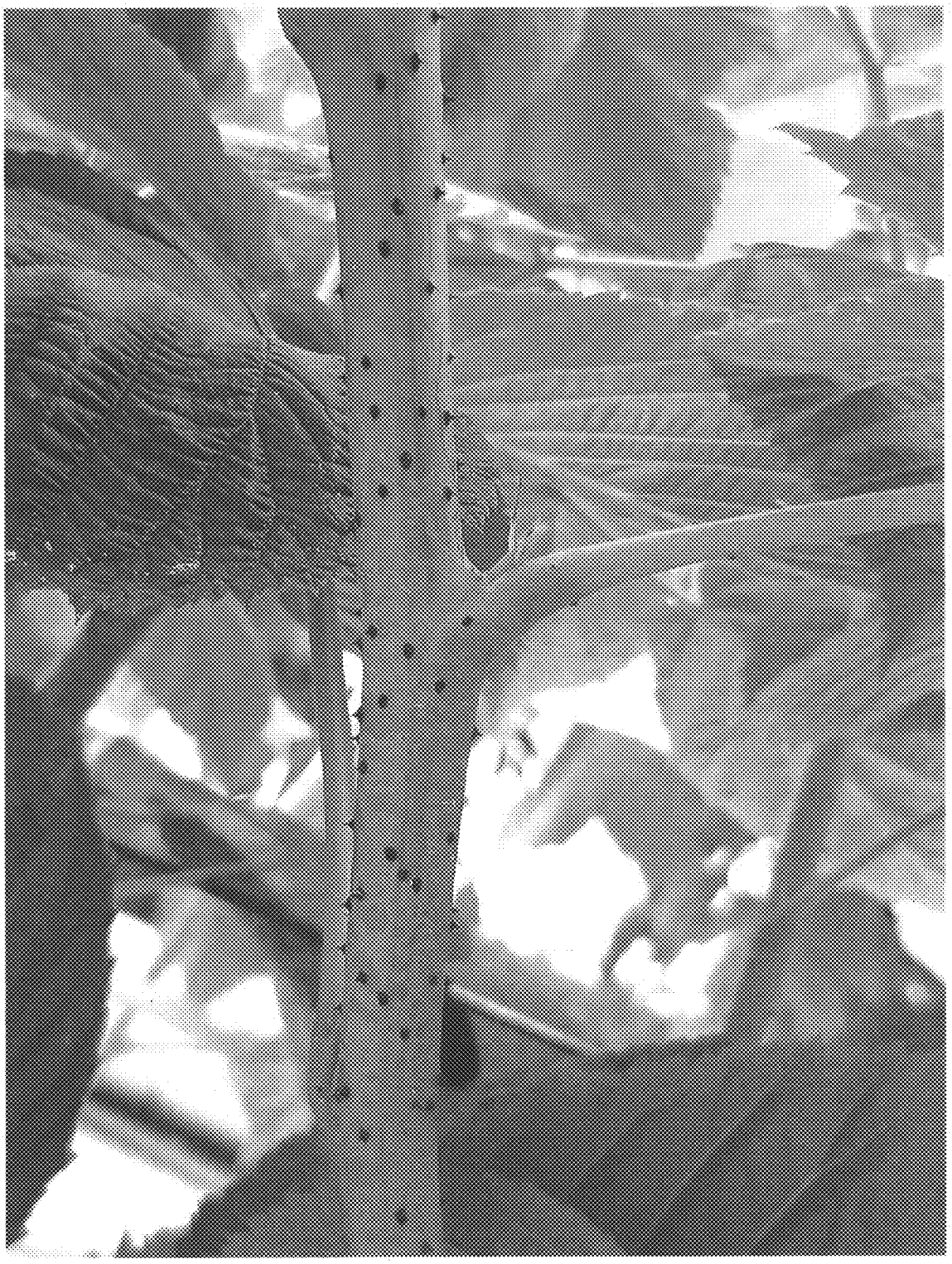
FIG. 2 shows current season's cane, 140 days after planting date.
Figure 3:
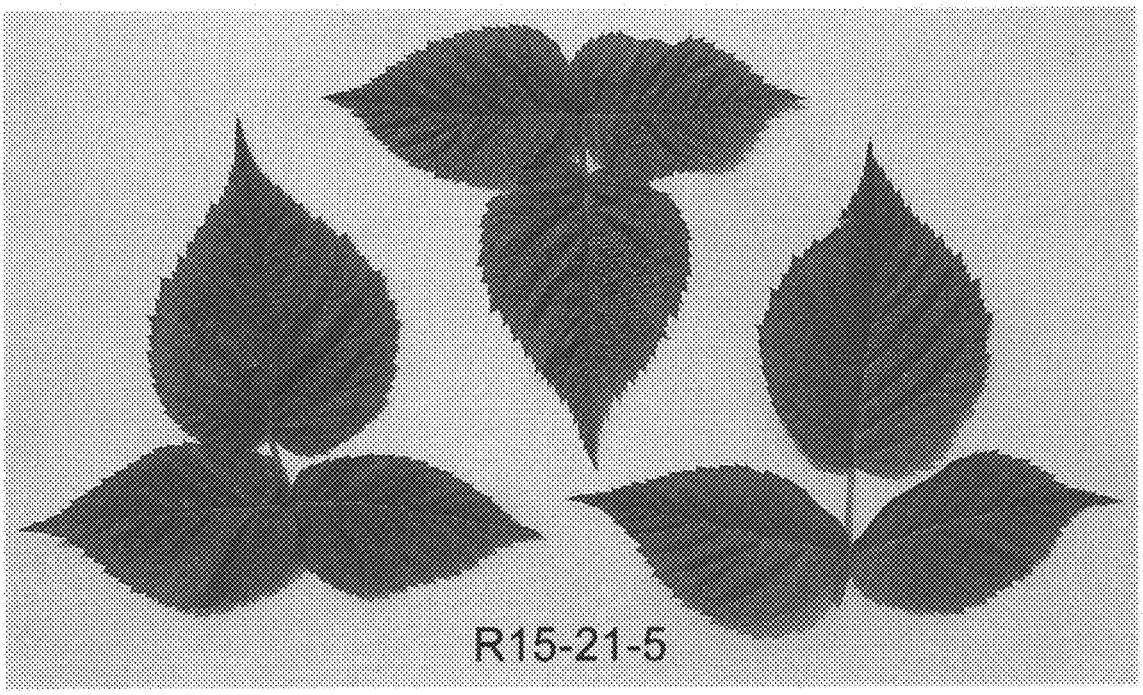
FIG. 3 shows the upperside leaves.
Figure 4:
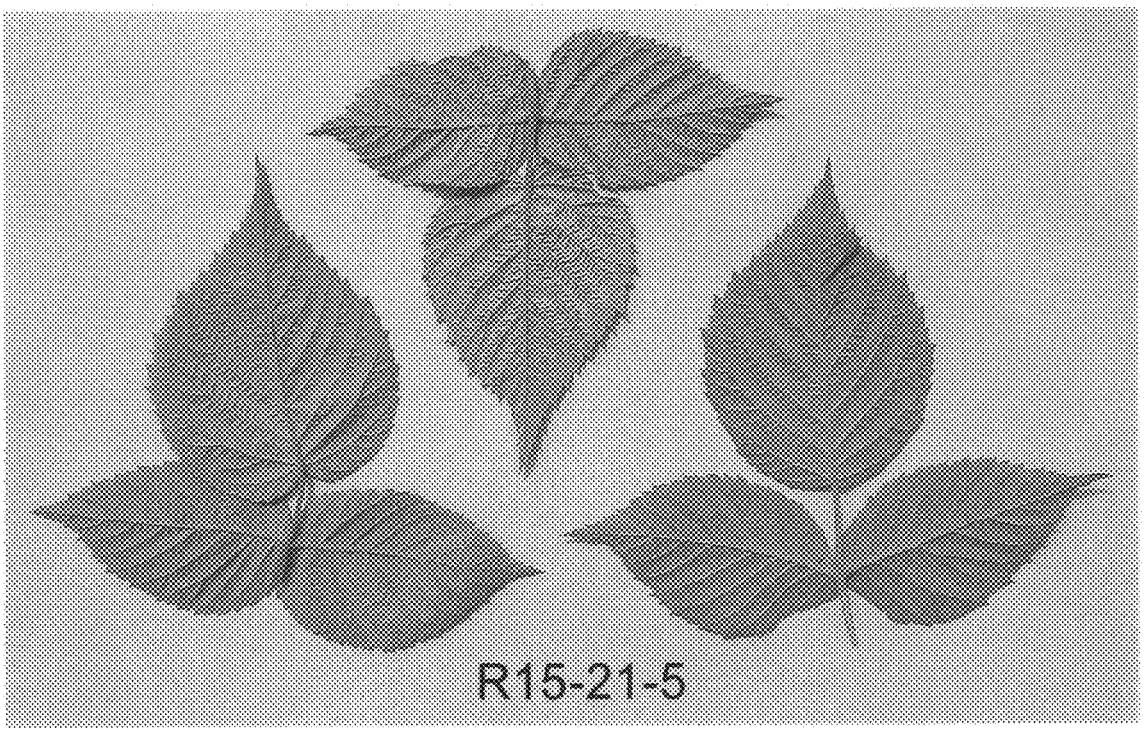
FIG. 4 shows the downside leaves.
Figure 5:
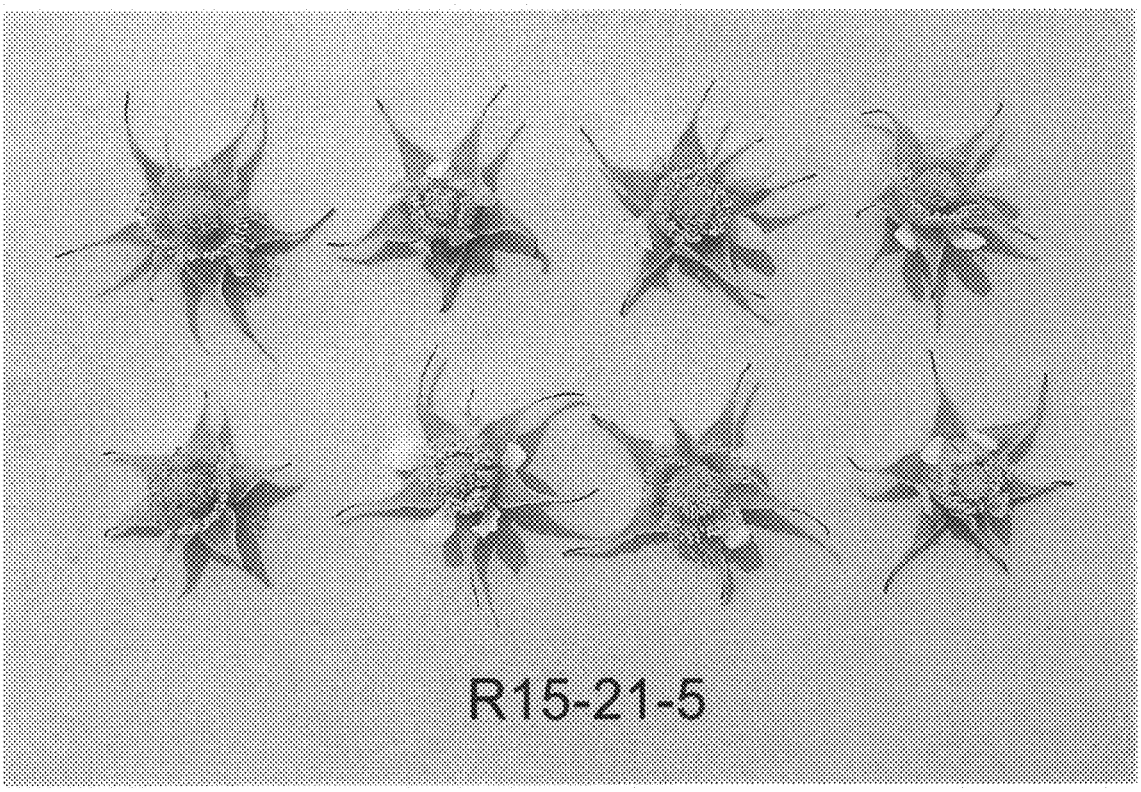
FIG. 5 shows the upperside flowers.
Figure 6:
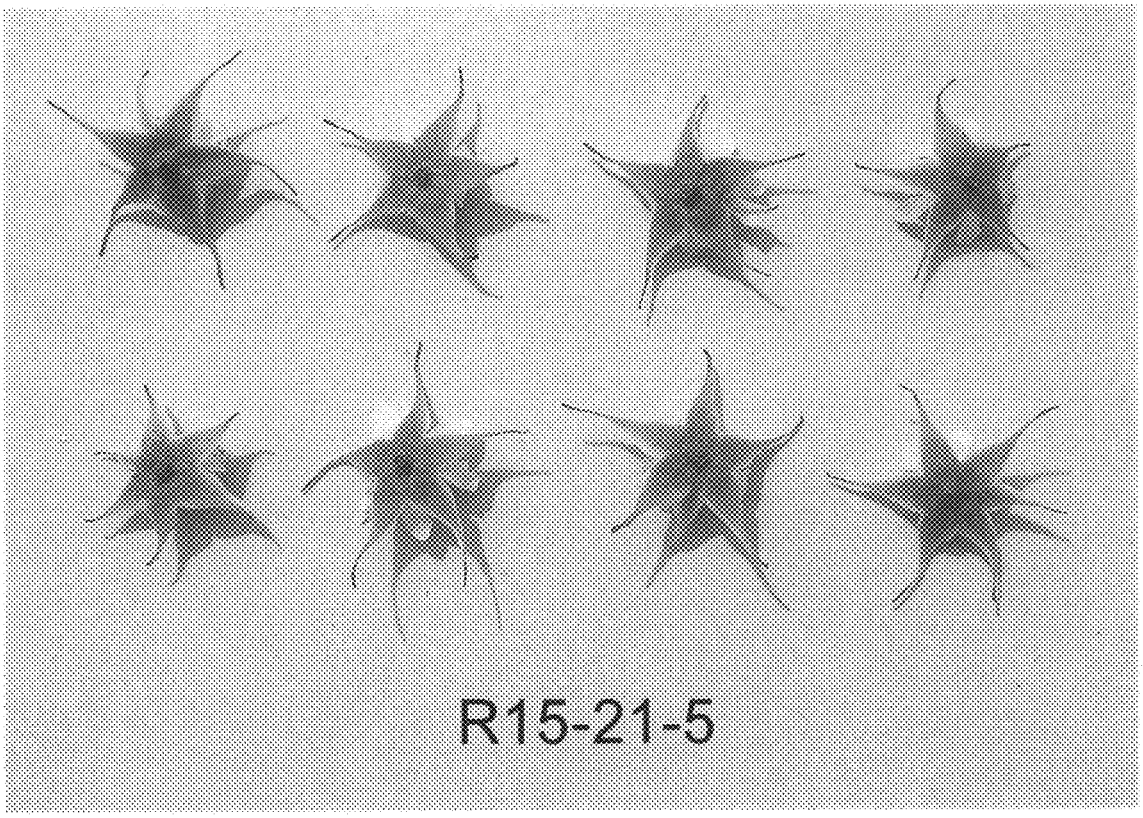
FIG. 6 shows the downside flowers.
Figure 7:
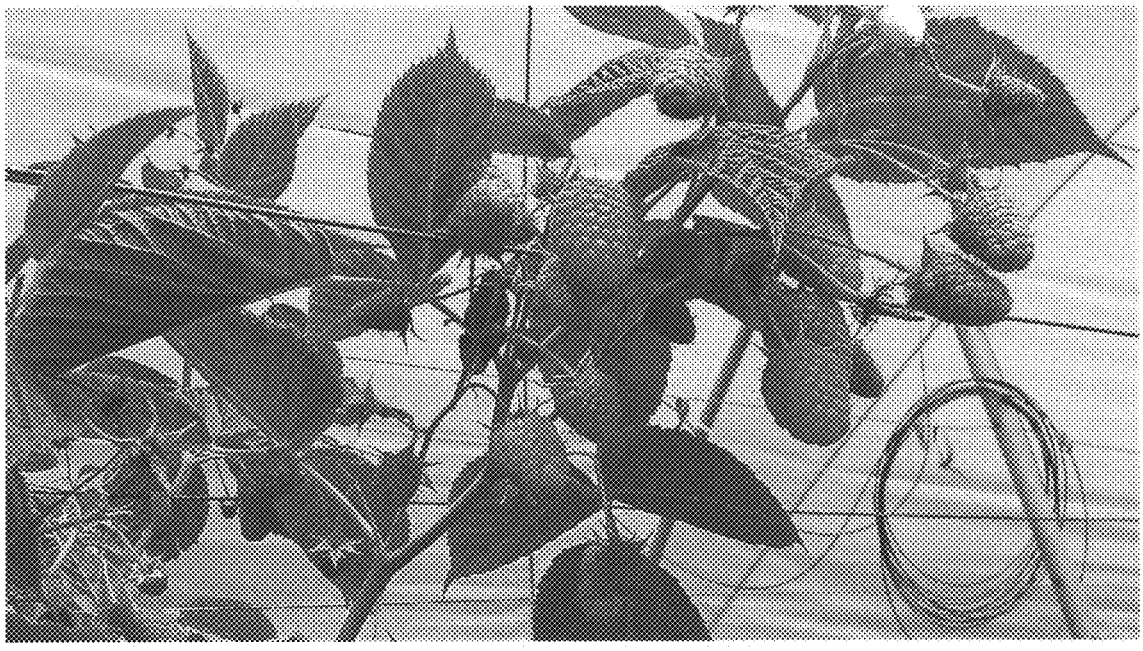
FIG. 7 shows the whole fruit on plant, 140 days after planting date.
Figure 8:
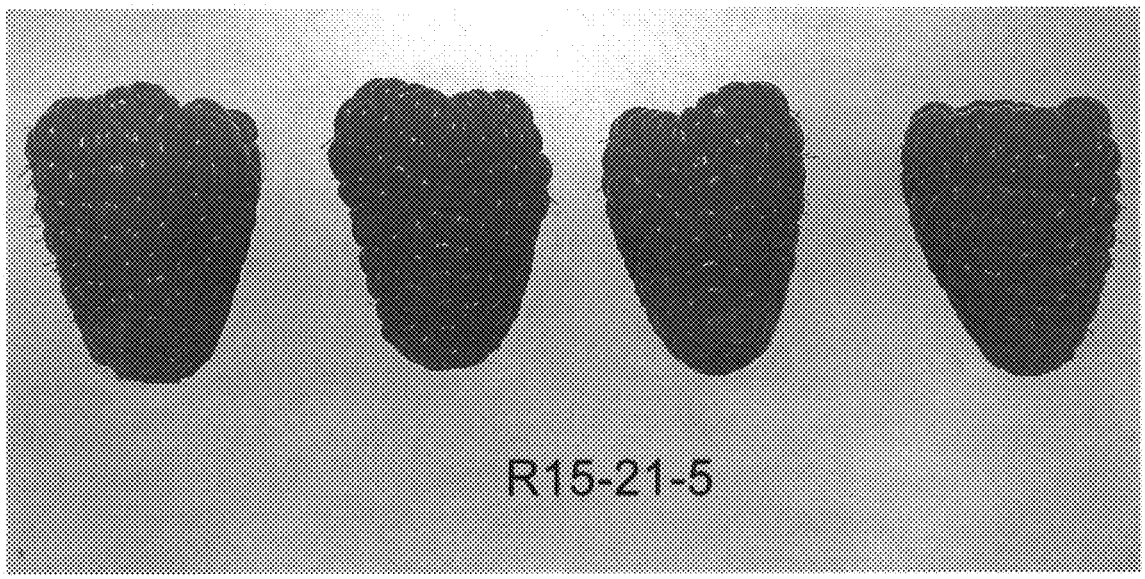
FIG. 8 shows the fruit in longitudinal cross-section, 140 days after planting date.
Figure 9:
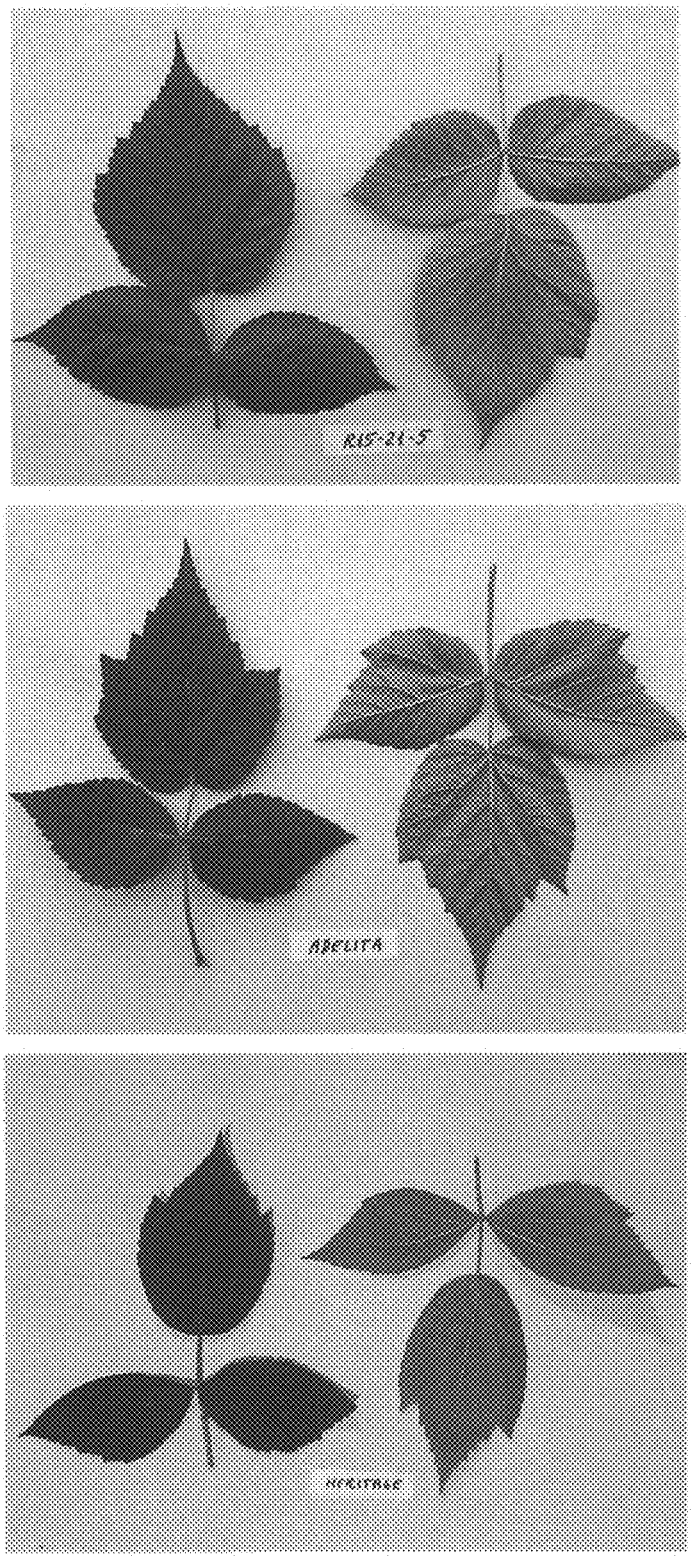
FIG. 9 shows the upperside and downside leaves of 'R15-21-5' compared with other commercial varieties.

Leaf. 'R15-21-5' is distinguished from other commercial cultivars such as 'Heritage' or 'Adelita' by the shape of the terminal leaflets (FIG. 9). Leaf rugosity in 'R15-21-5' is medium, which is more rugosity than that for 'Heritage' and less rugosity than that for 'Adelita' (FIG. 9). The green color of leaf upper side of 'R15-21-5' (RHS, NN137B to NN137C) is lighter than that for 'Adelita' (RHS, 138A to 137A) and 'Heritage' (RHS, 137A to NN137A) (FIG. 9).

Figure 10:
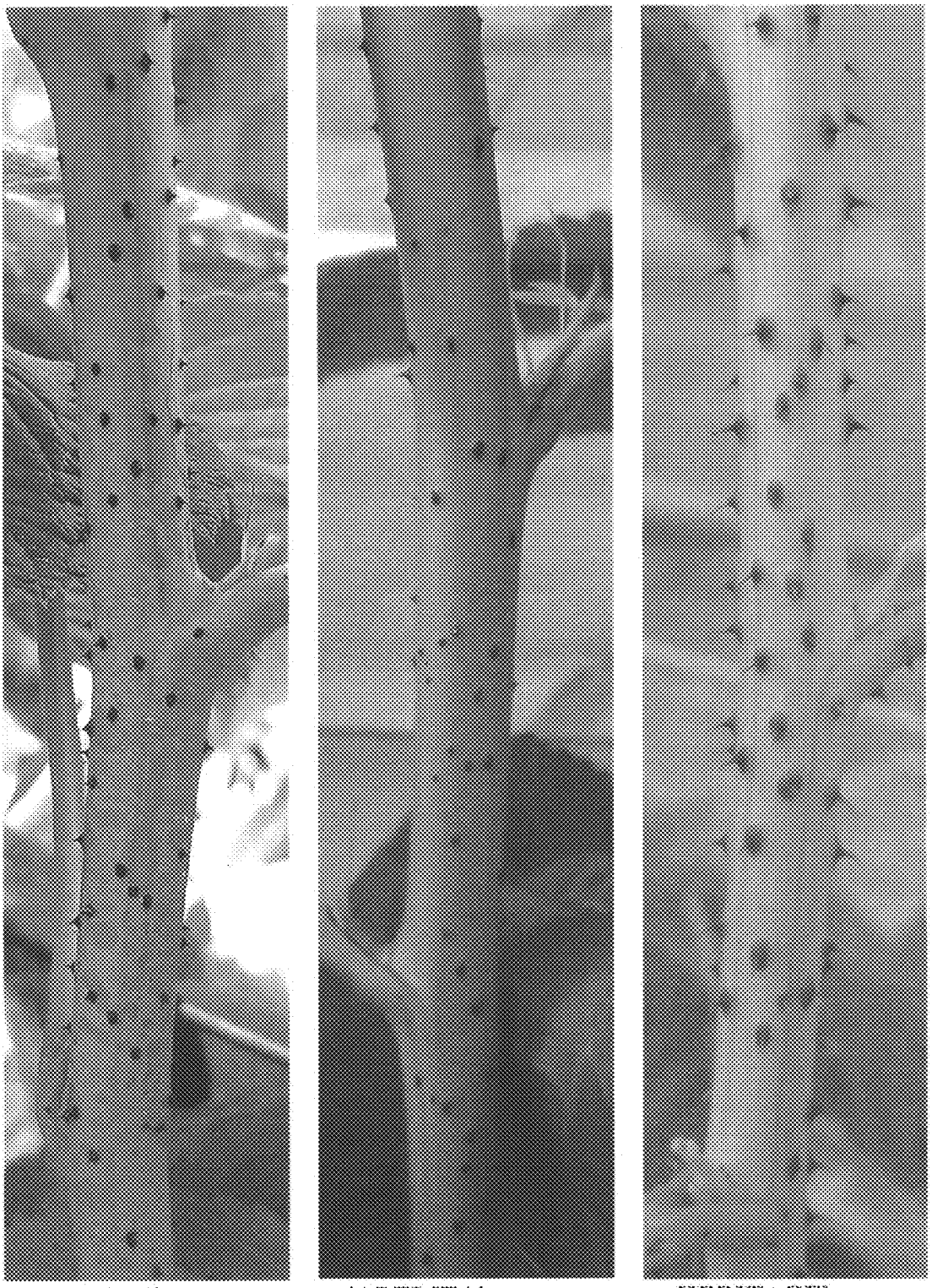
FIG. 10 shows cane of 'R15-21-5' compared with other commercial varieties 140 days after planting date.

Current season's cane. 'R15-21-5' shows glaucosity (Waxy Bloom) presence in canes and branches, meanwhile glaucosity (Waxy Bloom) in 'Adelita' is absent (FIG. 10). Cane color in 'R15-21-5' is near to RHS, 143B to 144A, whereas in 'Heritage' cane color is near to RHS, 142B to 142C.

Spines. 'R15-21-5' shows more spine density than 'Adelita' and less spine density than 'Heritage' in current season's cane (FIG. 10) and pedicel (FIG. 9).

Fruit. 'R15-21-5' shows a trapezoidal shaped fruit, meanwhile fruit shape in 'Adelita' is conical. In contrast, 'Heritage' shows a rounded general shape in fruit. 'R15-21-5' shows lighter red colored fruit (RHS, 46B to 46C) than 'Adelita' (RHS, 47A to 46A) and 'Heritage' (RHS, 59A to 59B).

The results provided below describe production, weight per fruit and Brix degrees of the variety 'R15-21-5' and commercial variety 'Adelita' (U.S. Plant Pat. No. 25,245 P3) from October 2016 to January 2017 on primocanes (Table 1) and from April 2017 to June 2017 on floricanes (Table 2). The results come from one trial located in Gibraleón (Huelva, Spain). The trial was a randomized complete block design with three repetitions and 6 plants per plot. Root cuttings were cultivated from Jul. 17, 2016 to May 31, 2017. It was cultivated under standard conditions of raspberry cultivation in Huelva, Spain.

TABLE 1

| Variety | Location | Cultivation method | Yield | brix | Weight |
|---|---|---|---|---|---|
| 'R15-21-5' | Gibraleón | Hydroponic | 1699 | 9.5 | 6.6 |
| 'Adelita' | Gibraleón | Hydroponic | 1126 | 9.0 | 6.9 |

Table 1. Fruit production, weight per fruit and Brix degrees of the varieties 'R15-21-5' and 'Adelita' from October 2016 to January 2017 on primocanes. Each value is the result of the average of three repetitions of 6 plants. yield, total commercial yield in grams per plant; weight, weight in grams per first quality fruits; brix, Brix degrees.

TABLE 2

| Variety | Location | Cultivation method | Yield | brix | weight |
|---|---|---|---|---|---|
| 'R15-21-5' | Gibraleón | Hydroponic | 1317 | 9.3 | 7.5 |
| 'Adelita' | Gibraleón | Hydroponic | 965 | 9.1 | 7.1 |

Table 2. Fruit production, weight per fruit and Brix degrees of the varieties 'R15-21-5' and 'Adelita' from April 2017 to June 2017 on floricanes. Each value is the result of the average of three repetitions of 6 plants. yield, total commercial yield in grams per plant; weight, weight in grams per first quality fruits; brix, Brix degrees.

The following traits in combination distinguish raspberry variety 'R15-21-5' from known raspberry varieties. It is based in UPOV terminology and color references are made to The Royal Horticultural Society Colour Chart, 2015 Edition, except where general terms of ordinary dictionary significance are used.

Following observations describe primocane variety with fruit production from October 2016 to January 2017 on primocanes and from end of April 2017 to June 2017 on floricanes, in 30-liter container in a greenhouse located in Huelva (Spain). Root cuttings were used for planting in July 2016.

TABLE 3

General.

| Characteristic | 'R15-21-5' |
|---|---|
| Main bearing type | Both, on previous year's cane and on current year's cane |
| Time of cane emergence | Early, 15 days from root summer planting date (July) |
| Time of beginning of flowering on current season's cane | Very early, 100 to 110 days from summer planting date (July) |
| Time of beginning of fruit ripening on current year's cane | Very early, 120 to 140 days from summer planting date (July) |
| Length of fruiting period on current year's cane | Long, 10 to 12 weeks from summer planting date (July) |

TABLE 4

Root.

| Characteristic | 'R15-21-5' |
|---|---|
| Habit | Dense |
| Thickness | Medium to thin |
| Color | RHS, 164A to 164B |

Observations made at the end of harvest on the current season's cane.

TABLE 5

Plant.

| Characteristic | 'R15-21-5' |
|---|---|
| Habit | Semi-upright |
| Vigor | Medium to high |
| Height | 190 to 200 cm |
| Width, plant diameter | 80 to 100 cm |

Observations made just before harvest on the current season's cane.

TABLE 6

Very young shoots.

| Characteristic | 'R15-21-5' |
|---|---|
| Anthocyanin coloration of apex during rapid growth | Absent |
| Color | RHS, 144B to 144C |

Observations made when the shoots are about 15 cm long.

TABLE 7

Current season's cane.

| Characteristic | 'R15-21-5' |
|---|---|
| Glaucosity (Waxy Bloom) | Present |
| Texture | Smooth |
| Anthocyanin coloration | Absent |
| Length of internode | Medium, 5.0 to 7.0 cm |
| Length of vegetative bud | Medium, 0.5 to 1.0 cm |
| Length | Long, 190 to 200 cm |
| Diameter | 1.28 to 1.36 cm |
| Color | RHS, 143B to 144A |

Observations made just before harvest, made in the middle third of the current season's cane.

TABLE 8

Lateral branches.

| Characteristic | 'R15-21-5' |
|---|---|
| Habit | Upright |
| Texture | Smooth |
| Glaucosity (Waxy Bloom) | Present |
| Anthocyanin coloration | Absent |
| Length of internode | Medium, 5.0 to 7.0 cm |
| Length | Long, 68 to 110 cm |
| Diameter | 0.68 to 0.87 cm |
| Color | RHS, 144B to 144C |

Observations made just before harvest, made in the middle third of the current season's cane.

TABLE 9

Spines.

| Characteristic | 'R15-21-5' |
|---|---|
| Presence | Present |
| Density | Sparse, 4.39/cm$^2$ |
| Size of base | Small, 0.10 to 0.20 cm |
| Length | Short, 0.20 to 0.30 cm |
| Shape | Deltoid |
| Color | RHS, 184A |

Observations on spines made in the middle third of the current season's cane.

TABLE 10

Petioles.

| Characteristic | 'R15-21-5' |
|---|---|
| Spines density | Very few, 5 to 8 |
| Length | 5.5 to 8.5 cm |

TABLE 10-continued

| Petioles. | |
|---|---|
| Characteristic | 'R15-21-5' |
| Color | RHS, 144B to 144C |
| Diameter | 0.30 to 0.37 cm |

Observations made on fully developed leaves from the middle third of the cane.

TABLE 11

| Stipules. | |
|---|---|
| Characteristic | 'R15-21-5' |
| Number per leaf | 2 |
| Length | 0.5 to 0.8 cm |
| Width | <0.1 cm |
| Shape | Erect |
| Color | RHS, 144B |

Observations made on fully developed leaves from the middle third of the cane.

TABLE 12

| Leaf. | |
|---|---|
| Characteristic | 'R15-21-5' |
| Color of upper side | RHS, NN137B to NN137C |
| Color of lower side | RHS, 148B |
| Venation pattern | Reticulate |
| Venation color | RHS, 143C |
| Predominant number of leaflets | 3 |
| Profile of leaflets in cross section | Concave |
| Rugosity | Medium |
| Relative position of lateral leaflets | Touching |
| Length | Long, 26.5 to 28.0 cm |
| Width | Broad, 28.0 to 30.5 cm |
| Shape | Unipinnate, Imparipinnate |
| Shape of tip | Acuminate |
| Shape of base | Rounded |
| Shape of margin | Serrate |
| Length of terminal leaflet | Long, 15.5 to 18.5 cm |
| Width of terminal leaflet | Broad, 14.5 to 16.5 cm |
| Length of lateral leaflet | Long, 14.5 to 15.3 cm |
| Width of lateral leaflet | Broad, 9.2 to 10.0 cm |
| Rachis length between terminal leaflet and adjacent lateral leaflets | Long, 4.5 to 5.5 cm |
| Rachis diameter | 3.5 to 4.5 cm |
| Rachis texture | Smooth |
| Rachis color | RHS, 144C |

Observations made on fully developed leaves from the middle third of the cane.

TABLE 13

| Pedicel. | |
|---|---|
| Characteristic | 'R15-21-5' |
| Number of spines on pedicel | Medium, 15 to 30 |
| Diameter | 0.11 to 0.13 cm |

TABLE 13-continued

| Pedicel. | |
|---|---|
| Characteristic | 'R15-21-5' |
| Length | 4.5 to 5.5 cm |
| Color | RHS, 143C to 144B |

Observations made during the autumn fruiting period.

TABLE 14

| Peduncles. | |
|---|---|
| Characteristic | 'R15-21-5' |
| Presence of anthocyanin coloration | Absent |
| Diameter | 0.18 to 0.25 cm |
| Length | 10 to 12 cm |
| Color | RHS, 143C to 144B |

Observations made during the autumn fruiting period.

TABLE 15

| Petals. | |
|---|---|
| Characteristic | 'R15-21-5' |
| Number per flower | 5 to 7 |
| Length | 0.5 to 0.6 cm |
| Width | 0.3 to 0.4 cm |
| Shape | Elliptic |
| Apex shape | Obcordate |
| Base shape | Acute |
| Margin shape | Entire |
| Petal texture of upper side | Smooth |
| Petal texture of lower side | Smooth |
| Petal color of upper side | RHS, NN155A to NN155B |
| Petal color of lower side | RHS, NN155A to NN155B |

Observations made during the autumn fruiting period.

TABLE 16

| Sepals. | |
|---|---|
| Characteristic | 'R15-21-5' |
| Number of sepals per flower | 5 |
| Length | 1.12 to 1.20 cm |
| Width | 0.5 to 0.7 cm |
| Shape | Deltoid |
| Apex shape | Aristate |
| Margin shape | Entire |
| Sepal texture of upper side | Smooth |
| Sepal texture of lower side | Smooth |
| Color of upper side | RHS, 143B to 143C |
| Color of lower side | RHS, 143A |

Observations made during the autumn fruiting period.

TABLE 17

| Flower. | |
|---|---|
| Characteristic | 'R15-21-5' |
| Size | Large |
| Depth | 0.9 to 1.2 cm |
| Diameter | 1.9 to 2.7 cm |

Observations made during the autumn fruiting period

TABLE 18

| Reproductive organs. | |
|---|---|
| Characteristic | 'R15-21-5' |
| Number of pistils/flower | 126 to 142 |
| Pistil length | 0.3 to 0.5 cm |
| Ovary shape | Oval |
| Ovary color | RHS, 144D |
| Style length | 0.3 to 0.4 cm |
| Style color | RHS, 155A |
| Number of stamens/flower | 102 to 116 |
| Stamen length | 0.4 to 0.6 cm |
| Stamen shape | Oval |
| Stamen color | RHS, 155A |
| Pollen color | RHS, 155B |

Observations made during the autumn fruiting period

TABLE 19

| Fruit. | |
|---|---|
| Characteristic | 'R15-21-5' |
| Length | Long, 2.6 to 3.0 cm |
| Width | Broad, 2.5 to 2.8 cm |

TABLE 19-continued

| Fruit. | |
|---|---|
| Characteristic | 'R15-21-5' |
| Ratio length/width | Large |
| General shape in lateral view | Trapezoidal |
| Size of single drupe | Large, 0.3 to 0.4 cm |
| Color | RHS, 46B to 46C |
| Glossiness | Strong |
| Firmness | Firm |
| Adherence to plug | Very weak |
| Number of drupelets | 124 to 148 |
| Diameter hollow center | 0.9 to 1.1 cm |

Observations made on fruit picked during the second and third harvest of the autumn fruiting period.

Storage capacity. Fruits are suitable for fresh consumption with excellent quality and high firmness. 'R15-21-5' fruit maintains quality characteristics when it is kept in a refrigerated chamber, such as a Frigo® Zika refrigeration chamber, with temperatures ranging from 2° C. to 4° C. for three days.

Temperature tolerance. 'R15-21-5' plants are suitable to be cultivated to USDA Hardiness Zone '9b'.

The invention claimed is:

1. A new and distinct cultivar of raspberry plant named 'R15-21-5' as described and shown herein.

* * * * *

'R15-21-5' 'ADELITA' HERITAGE'